United States Patent
Inui et al.

(10) Patent No.: US 10,413,717 B2
(45) Date of Patent: Sep. 17, 2019

(54) PAIN SENSORY NERVE STIMULATION APPARATUS

(75) Inventors: Koji Inui, Okazaki (JP); Yasuyuki Takeshima, Okazaki (JP); Jun Motogi, Tokyo (JP); Yoshinobu Ono, Tokyo (JP); Takeshi Kojima, Tokyo (JP); Ryosuke Ushijima, Tokyo (JP); Katsumi Nakaichi, Tokyo (JP); Kazuwa Shibuya, Tokyo (JP)

(73) Assignees: INTER-UNIVERSITY RESEARCH INSTITUTE CORPORATION NATIONAL INSTITUTES OF NATURAL SCIENCES, Tokyo (JP); NIHON KOHDEN CORPORATION, Tokyo (JP)

( * ) Notice: Subject to any disclaimer, the term of this patent is extended or adjusted under 35 U.S.C. 154(b) by 1158 days.

(21) Appl. No.: 12/570,213

(22) Filed: Sep. 30, 2009

(65) Prior Publication Data
US 2010/0094378 A1    Apr. 15, 2010

(30) Foreign Application Priority Data

Oct. 10, 2008   (JP) ................................. 2008-264298

(51) Int. Cl.
*A61N 1/36* (2006.01)
*A61N 1/04* (2006.01)
*A61B 5/04* (2006.01)
*A61B 5/00* (2006.01)
*A61N 1/05* (2006.01)

(52) U.S. Cl.
CPC ........ *A61N 1/0456* (2013.01); *A61B 5/04001* (2013.01); *A61B 5/4824* (2013.01); *A61N 1/0472* (2013.01); *A61N 1/36017* (2013.01); *A61N 1/36021* (2013.01); *A61N 1/0502* (2013.01)

(58) Field of Classification Search
CPC ................. A61N 1/36017; A61N 1/36021
USPC ........................................... 607/46
See application file for complete search history.

(56) References Cited

U.S. PATENT DOCUMENTS 5,395,398 A * 3/1995 Rogozinski ................. 607/50
5,755,750 A * 5/1998 Petruska et al. ............. 607/75
(Continued)

FOREIGN PATENT DOCUMENTS

JP          3543097 B2    7/2004
WO      2005/023361 A2    3/2005
(Continued)

OTHER PUBLICATIONS

English Translation of WO 2006/059430.*
(Continued)

*Primary Examiner* — Eric D. Bertram
(74) *Attorney, Agent, or Firm* — Sughrue Mion, PLLC (57) ABSTRACT

A pain sensory nerve stimulation apparatus includes: an electrode portion including: a first electrode, a tip end of which is adapted to be inserted into a skin; and at lease one second electrode which is disposed in a circumference of the first electrode without being electrically conductive with the first electrode, and which is adapted to be in contact with a skin; and a pulse signal supplier, supplying a pulse signal in which an electrical polarity of the first electrode is set as a anode and an electrical polarity of the second electrode is set as a cathode.

16 Claims, 10 Drawing Sheets

(56) References Cited

U.S. PATENT DOCUMENTS

| | | | |
|---|---|---|---|
| 5,806,522 A | 9/1998 | Katims | |
| 6,631,294 B2 * | 10/2003 | Andino et al. | 607/46 |
| 9,662,063 B2 * | 5/2017 | Inui | A61B 5/4824 |
| 2006/0085056 A1 * | 4/2006 | Schouenborg | 607/148 |

FOREIGN PATENT DOCUMENTS

| | | | | |
|---|---|---|---|---|
| WO | 2006-059430 A1 | 6/2006 | | |
| WO | WO 2006/059430 A1 * | 6/2006 | | A61B 5/04 |

OTHER PUBLICATIONS

Extended European Search Report dated Feb. 1, 2010 in European Application No. 09171430.3-2305, 6 pages.
Office Action dated Jun. 27, 2013 issued by the Japanese Patent Office in counterpart Japanese Patent Application No. 2008-264298.
Noriko Ichiishi et al; "A New Electrode and Analysis of Discrimination of Painful Electrical Stimuli"; The Japanese Journal of Anesthesiology; vol. 36, No. 8; Aug. 1987; pp. 1168-1172; 8 sheets.
Chinese Office Action dated Jun. 4, 2012, In Application No. 200910178137.5.
Shen Qiang, et al., "Selective Stimulation of Mammalian Nerve Fibers Using Biphasic Pulses", Journal of XI' AN Jiaotong University, vol. 34, No. 2, Feb. 2000, pp. 52-57.
Communication dated Feb. 5, 2015 by the State Intellectual Property Office in related application No. 200910178137.5.
Office Action dated Jun. 29, 2015, issued by the Intellectual Property Office of the People's Republic of China in counterpart Chinese Patent Application No. 200910178137.5.

* cited by examiner

ABSCISSA: 200 μs
ORDINATE: 0.1 mA
PULSE DURATION: 0.5 ms

EFFECTIVE REGION OF C FIBER STIMULATION 0.11~0.25 mA 0.06~0.29 mA

FIG. 9E

| PULSE WAVEFORM | THRESHOLD OF C FIBER STIMULATION AT 0.02 mA | THRESHOLD OF C FIBER STIMULATION AT 0.03 mA | THRESHOLD OF C FIBER STIMULATION AT 0.04 mA | THRESHOLD OF C FIBER STIMULATION AT 0.05 mA |
|---|---|---|---|---|
| SQUARE WAVE | 40 μA × ms | 48 μA × ms | 40 μA × ms | 40 μA × ms |
| RECTILINEARLY RISING PULSE WAVE | 36 μA × ms | 39 μA × ms | 40 μA × ms | 40 μA × ms |
| EXPONENTIALLY RISING PULSE WAVE | 32 μA × ms | 36 μA × ms | 36 μA × ms | 40 μA × ms |

FIG. 9F

| PULSE DURATION | 1 | 3 | 5 | 10 | 20 | 30 | 40 | 50 | 60 | 70 | 80 | (ms) |
|---|---|---|---|---|---|---|---|---|---|---|---|---|
| THRESHOLD OF C FIBER STIMULATION | N/A | N/A | N/A | N/A | 0.08 | 0.06 | 0.05 | 0.05 | 0.05 | 0.04 | 0.04 | (mA) |

FIG. 9G

| PULSE NUMBER | 1 | 2 | 3 | 5 | 7 | 10 | |
|---|---|---|---|---|---|---|---|
| THRESHOLD OF C FIBER STIMULATION | N/A | N/A | 0.05 | 0.05 | 0.05 | 0.05 | (mA) |

FIG. 10

PAIN SENSORY NERVE STIMULATION APPARATUS

BACKGROUND OF THE INVENTION

The present invention relates to a pain sensory nerve stimulation apparatus which, with respect to sharp or first pain produced by stimulation of Aδ fibers and dull or second pain produced by stimulation of C fibers, can stimulate C fibers selectively.

In order to selectively evoke pain sensations by electrical stimulation, an electrode disclosed in WO2006/059430 has been developed. According to the electrode, it is possible to stimulate Aδ fibers (see FIG. 4 of WO2006/059430).

By contrast, in order to detect disorders of the peripheral nerve at its early stages that is one of the three major complications of diabetes mellitus, a method by which C fibers are selectively stimulated and responses to the stimulation are measured is highly requested. This is based on that C fibers have a nerve diameter of 0.4 to 1.2 μm, Aδ fibers have a diameter of 2 to 5 μm, and Aβ fibers which are connected to mechanoreceptors relating to touch pressure sensations, have a diameter of 5 to 12 μm, and that a peripheral nervous disorder often begins from small fibers. When it is possible to stimulate C fibers which are smaller than Aδ fibers that can be stimulated by the electrode disclosed in WO2006/059430, therefore, development of a nervous disorder can be known earlier, thereby largely contributing to knowing of progression of and adequate control of a diabetic nervous disorder. In a related-art technique of selective stimulating C fibers, a laser apparatus is used. In the case where a laser apparatus is used, however, large-scale testing equipment and facility are required, and the size, cost, and complexity of the apparatus are increased to cause a problem of versatility. The accuracy of C fiber stimulation by laser beams has not yet reached to a satisfactory level, and the probability of C fiber stimulation is low. Therefore, a laser apparatus has not been used in a clinical application.

Also in WO2006/059430, when stimulation is applied while a needle terminal of the stimulation electrode is set as a cathode and the surrounding electrode is set as a anode, it is possible to selectively stimulate Aδ fibers, but C fibers cannot be selectively stimulated.

Figure 10:
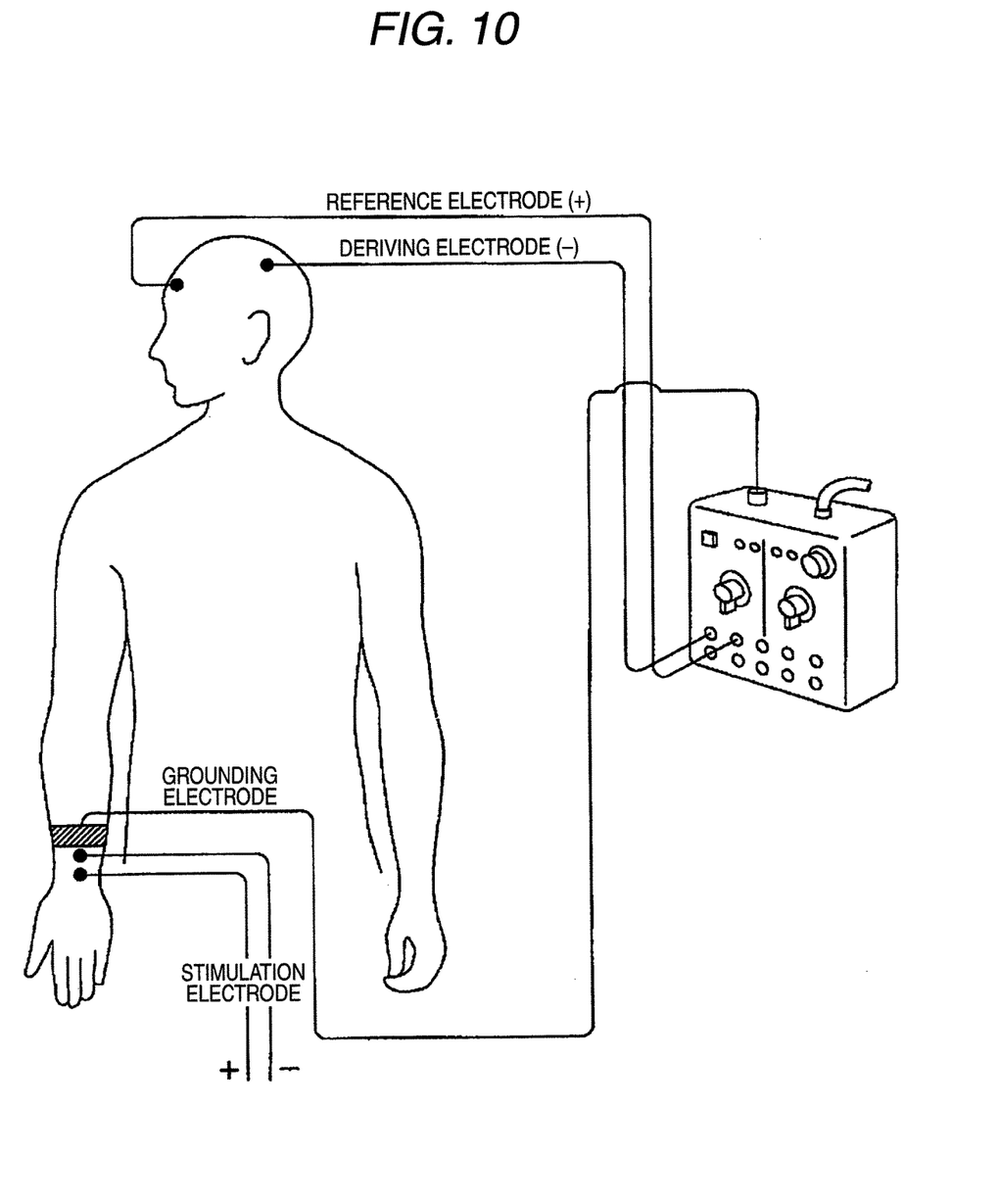
FIG. 10 is a view showing an arrangement of electrodes with respect to a living body in a measurement of the somatosensory evoked potentials SEPs.

In the field of the art, a related-art technique in which electrical stimulation of the negative polarity is applied to a stimulus-intended electrode attached to a desired stimulation portion, and the positive polarity is applied to a terminal electrode is usually employed because excitation of peripheral nerves is generated immediately below a stimulation electrode of the negative polarity. Also WO2006/059430 discloses that stimulation is applied while the needle electrode of the stimulation electrode is set as a cathode and the surrounding electrode is set as a anode, so that Aδ fibers can be selectively stimulated. However, it is well known in the field that, even when the electrical polarity is inverted, the inversion exerts no effect or influence on nerve stimulation from the skin surface which is used in a measurement of the somatosensory evoked potentials (SEPs) (see FIG. 10).

A related-art apparatus which automatically measures in an electrophysiologic or quantitative manner the electrical current perceptive threshold and the algestic tolerant threshold is known (see U.S. Pat. No. 5,806,522). In the related-art apparatus, stimulation is applied by using a sine wave, and C fibers, Aδ fibers, and Aβ fibers are most responsive to stimulation of frequencies of 5 Hz, 250 Hz, and 2,000 Hz, respectively. U.S. Pat. No. 5,806,522 does not disclose a technique in which C fibers, Aδ fibers, and Aβ fibers can be independently stimulated. In the related-art apparatus, stimulation due to a sine wave is required. Therefore, the related-art apparatus is complicated in structure for producing and controlling stimulation, as compared with the case where stimulation is applied by a pulse wave which is typified by a square wave.

The related-art apparatus disclosed in U.S. Pat. No. 5,806,522 uses a surface electrode, and hence the stimulation intensity to be applied is larger than the case where an electrode is inserted into the skin. In stimulation of small fibers such as C fibers, namely, there is a large possibility that also other nerve fibers such as tactile fibers are stimulated. Therefore, it is considered that selective stimulation of C fibers is difficult. Since stimulation due to a sine wave is applied, stimulation for 3 seconds must be applied two times in stimulation of C fibers (see Columns 8 and 9 of U.S. Pat. No. 5,806,522). During the measurement, the subject suffers from pain. Stimulation of C fibers can be known by calculating the conduction velocity by use of SEPs. In view of the fact that the conduction velocity in nerve fibers is about several m/s, when stimulation is performed for several seconds as in the related-art apparatus disclosed in U.S. Pat. No. 5,806,522, responses to the stimulation cannot be obtained, therefore, it is considered that identification of which nerve fibers are stimulated is impossible.

Japanese Patent No. 3,543,097 discloses a related-art apparatus in which specific tactile sensory receptors are selectively stimulated by using a surface electrode without evoking pain sensations. This related-art apparatus is effective in stimulating the tactile sensations. Since the surface electrode is used, however, the stimulation intensity is as large as about 2 mA as described before. Furthermore, Aδ fibers and C fibers which relate to the pain sensations are small fibers, and hence stimulation is hardly performed. In the related-art apparatus disclosed in Japanese Patent No. 3,543,097, therefore, it is impossible to selectively stimulate Aδ fibers and C fibers. The related-art apparatus disclosed in Japanese Patent No. 3,543,097 has a further problem in that a complex process such as a weighted change is required in selective stimulation of receptors.

In usual electrical stimulation, excitation is more easily caused in the sequence of Aβ fibers, Aδ fibers, and C fibers. Namely, electrical stimulation is more easily performed on thickly myelinated fibers, and excitation due to electrical stimulation most hardly occurs in C fibers that are small in diameter and unmyelinated. Therefore, stimulation of C fibers without affecting other fibers has been very difficult.

SUMMARY

It is therefore an object of the invention to provide a simple pain sensory nerve stimulation apparatus which can stimulate only C fibers by electrical stimulation in a short period of time. It is another object of the invention to provide a pain sensory nerve stimulation apparatus which can independently stimulate both C fibers and Aδ fibers.

In order to achieve the object, according to the invention, there is provided a pain sensory nerve stimulation apparatus comprising:
  an electrode portion including:
    a first electrode, a tip end of which is adapted to be inserted into a skin; and
    at lease one second electrode which is disposed in a circumference of the first electrode without being electrically conductive with the first electrode, and which is adapted to be in contact with the skin surface; and a pulse signal supplier, supplying a pulse signal in which an electrical polarity of the first electrode is set as anode and an electrical polarity of the second electrode is set as cathode.

The pain sensory nerve stimulation apparatus may further include a rise/fall time controller, changing at least one of a rise time and a fall time of the pulse signal.

At least one of rising and falling of the pulse signal may be changed so as to have a rectilinear inclined shape.

At least one of rising and falling of the pulse signal may be changed so as to have an exponential shape.

The pain sensory nerve stimulation apparatus may further include a stimulation intensity controller, changing at least one of a voltage and a current of the pulse signal.

The pain sensory nerve stimulation apparatus may further include a pulse waveform controller, changing at least one of a pulse duration, a pulse interval, and a pulse number of the pulse signal.

The pulse signal may have a pulse duration of 0.1 to 100 ms.

A region surrounded by a waveform shape of the pulse signal and a time axis may have an area of 0.01 to 100 (ms·mA).

A region surrounded by a waveform shape of the pulse signal and a time axis may have an area of 0.1 to 20,000 (ms·V).

The pain sensory nerve stimulation apparatus may further include an electrical polarity converter, converting between the electrical polarity of the first electrode and the electrical polarity of the second electrode.

The second electrode may be annularly disposed in the circumference of the first electrode.

The pain sensory nerve stimulation apparatus may include a plurality of the electrode portion.

DETAILED DESCRIPTION OF EMBODIMENTS

Figure 1:
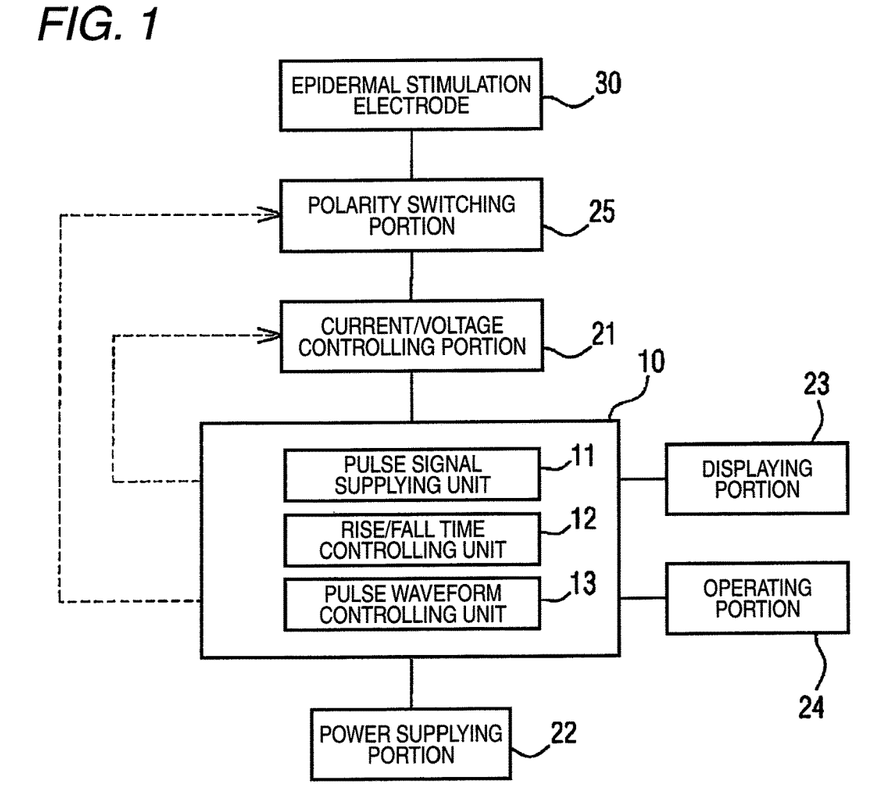
FIG. 1 is a block diagram showing the configuration of an embodiment of a pain sensory nerve stimulation apparatus of the present invention.

Hereinafter, the pain sensory nerve stimulation apparatus of the invention and examples of a method of using the apparatus will be described with reference to the accompanying drawings. In the pain sensory nerve stimulation apparatus, as shown in FIG. 1, a current/voltage controlling portion 21, a power supplying portion 22, a displaying portion 23, and an operating portion 24 are connected to a pulse generation main unit 10. A polarity switching portion 25 is connected to the current/voltage controlling portion 21, and an intraepidermal stimulation electrode portion 30 is connected to the polarity switching portion 25.

Figure 2A:
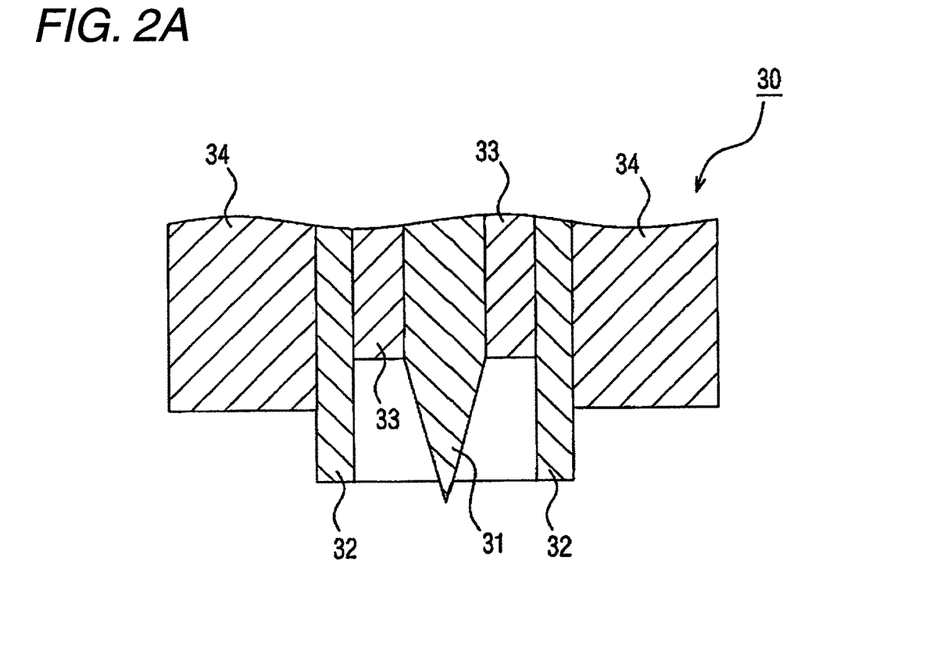
FIG. 2A is a sectional view showing electrodes used in the embodiment of the pain sensory nerve stimulation apparatus.
Figure 2B:
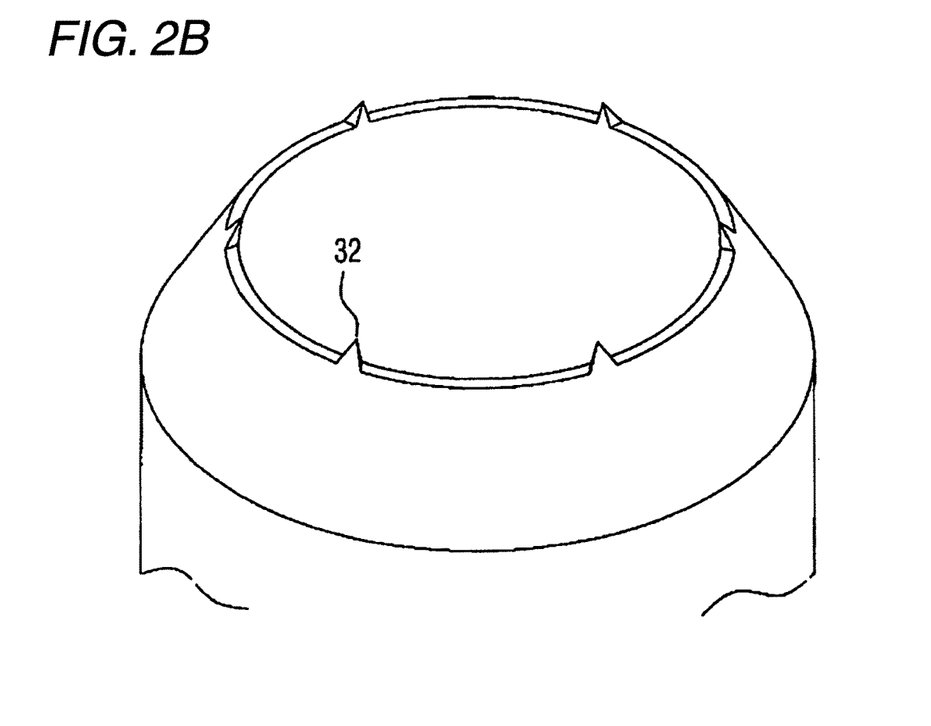
FIG. 2B is a perspective view showing an example of the electrodes used in the embodiment of the pain sensory nerve stimulation apparatus.

The intraepidermal stimulation electrode portion 30 is structured in a substantially same manner as the electrode disclosed in WO2006/059430. FIG. 2A is a sectional view of the portion. The intraepidermal stimulation electrode portion 30 includes: a needle electrode 31 in which the tip end has a shape that allows the tip end to be slightly inserted into the skin; and a contact electrode 32 which is to be used while being in contact with the skin. As seen from FIG. 2, the needle electrode 31 is projected with respect to the contact electrode 32. The tip end of the needle electrode 31 is not always necessary to be pointed, and may have a spherical or rod-like shape. The contact electrode 32 may have a cylindrical shape which surrounds the needle electrode 31 while being centered at the needle electrode 31, or alternatively a plurality of contact electrodes 32 may be cylindrically placed so as to be centered at the needle electrode 31. The contact electrode has an inner diameter of, for example, 1 mm. As shown in FIG. 2B, a part of the contact electrode 32 may have a shape which enables the part to be slightly inserted into the skin.

A spacer 33 configured by an insulating material may be embedded in the gap between the contact electrode 32 and the needle electrode 31. An external fitting portion 34 which has a columnar shape using the contact electrode 32 as a core, and which is formed by an insulating material is disposed in the circumference of the contact electrode 32.

Figure 3:
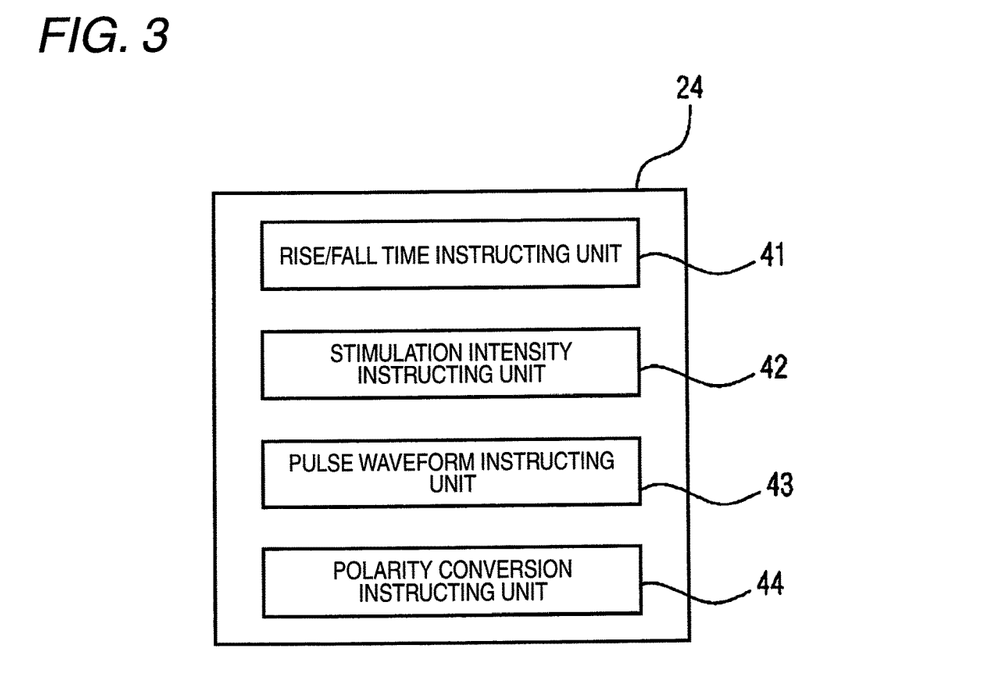
FIG. 3 is a block diagram showing the configuration of the embodiment of the pain sensory nerve stimulation apparatus.
Figure 9A:
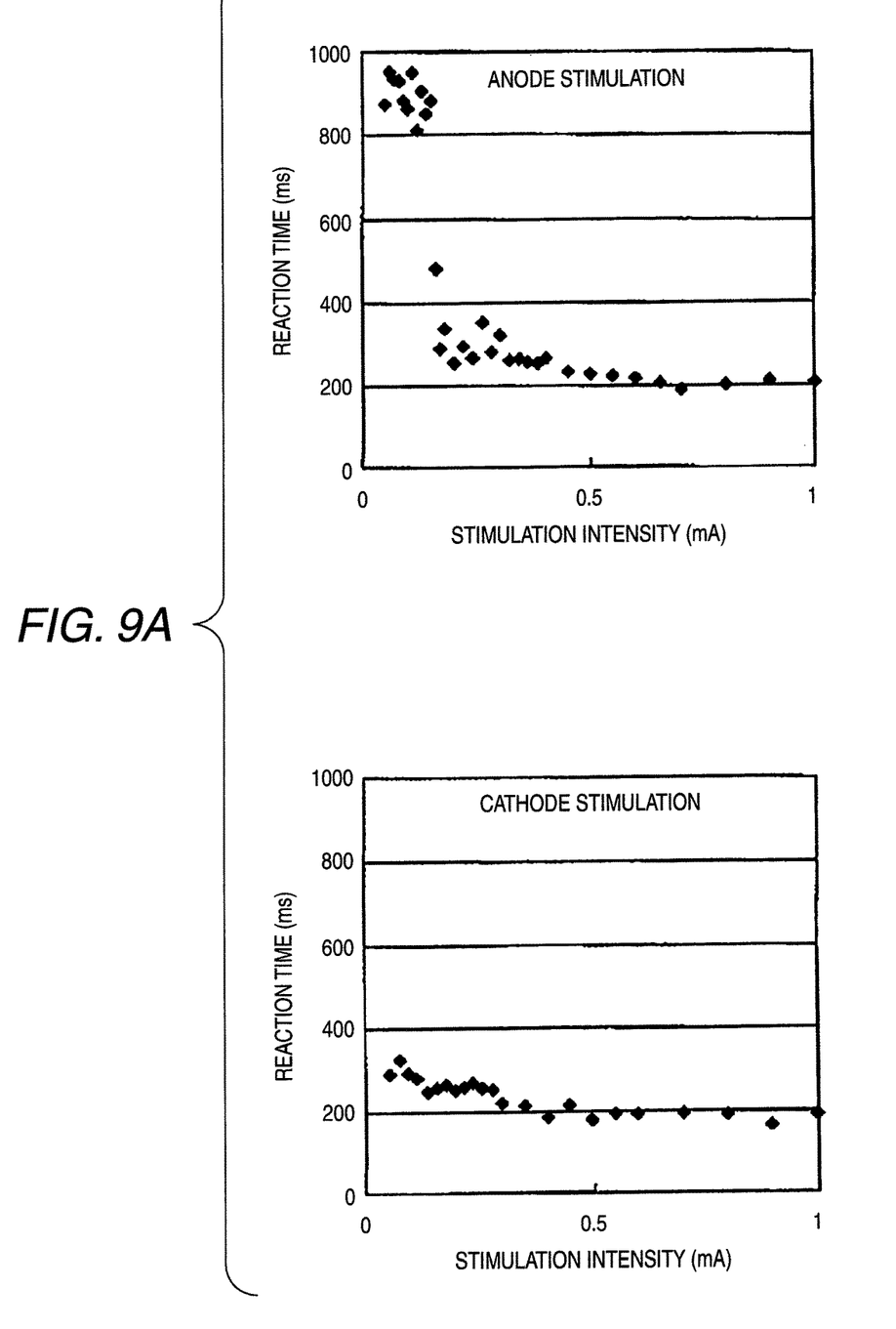
FIG. 9A is a view showing relationships between electrical polarities and stimulation intensity in the pain sensory nerve stimulation apparatus.

The pulse generation main unit 10 is configured by an analog/digital microprocessor, and includes a pulse signal supplying unit 11 which generates and supplies a pulse signal, a rise/fall time controlling unit 12, and a pulse waveform controlling unit 13. The rise/fall time controlling unit 12 changes at least one of the rise and fall times of the pulse signal supplied from the pulse signal supplying unit 11. The operating portion 24 may be configured by dials, buttons, a keyboard, a touch panel, or the like, and, as shown in FIG. 3, includes a rise/fall time instructing unit 41. The rise/fall time instructing unit 41 can give an instruction input for changing the rise and fall times of the pulse signal to a desired one, to the rise/fall time controlling unit 12. Furthermore, the rise/fall time controlling unit 12 can select either of a rectilinear mode where the rise and fall of the pulse signal have rectilinearly rising and falling shapes, and an exponential mode where the rise and fall of the pulse signal have exponentially rising and falling shapes, so that pulse waveforms of shapes such as shown in FIG. 9E can be produced.

Figure 4A:
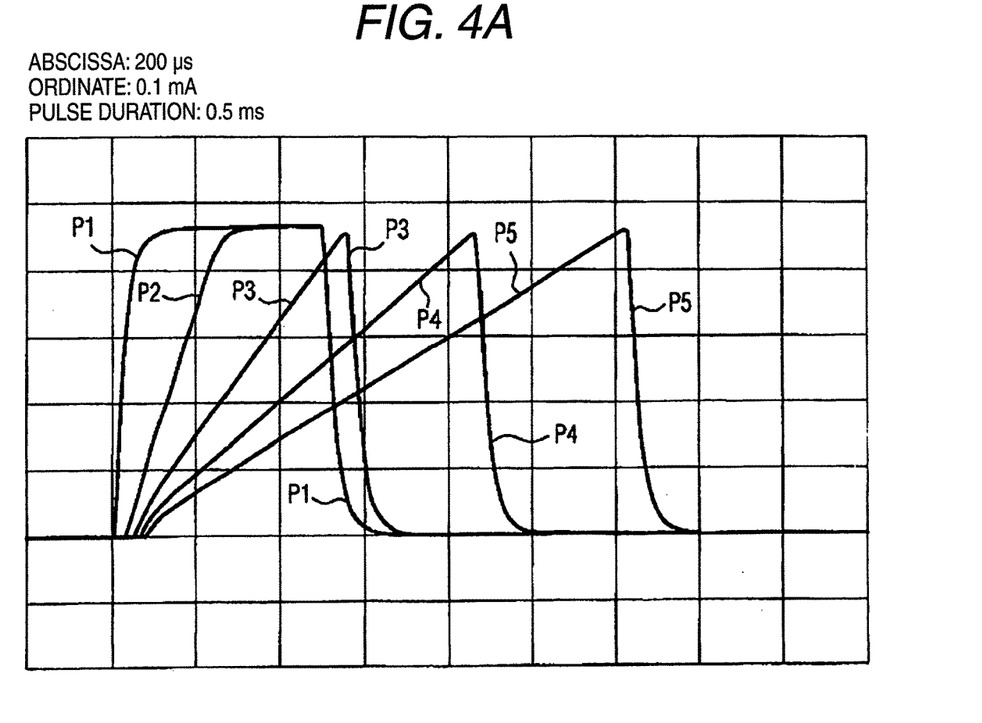
FIG. 4A is a view showing waveforms of pulse signals which are supplied in the embodiment of the pain sensory nerve stimulation apparatus, and in which rise times of the pulse signals are made different.

In the instruction input from the rise/fall time instructing unit 41, the rise time and the fall time can be designated. For example, a desired pulse in which the rise time is 0.068 ms to 1,000 ms and the fall time is 0.068 ms to 5 ms can selected. Furthermore, also the rising and falling shapes can be designated. In the rectilinear mode where the pulse rectilinearly rises/falls, and the exponential mode where exponentially rises/falls, for example, a desired rising/falling shape can be selected. FIG. 4A shows five kinds of pulses P1 to P5 in which the fall time is set to 0.068 ms and the rise time is set to 0.068 ms, 0.34 ms, 0.68 ms, 1.02 ms, and 1.36 ms. As seen from the above, pulses include not only a square wave but also a sawtooth wave.

Figure 4B:
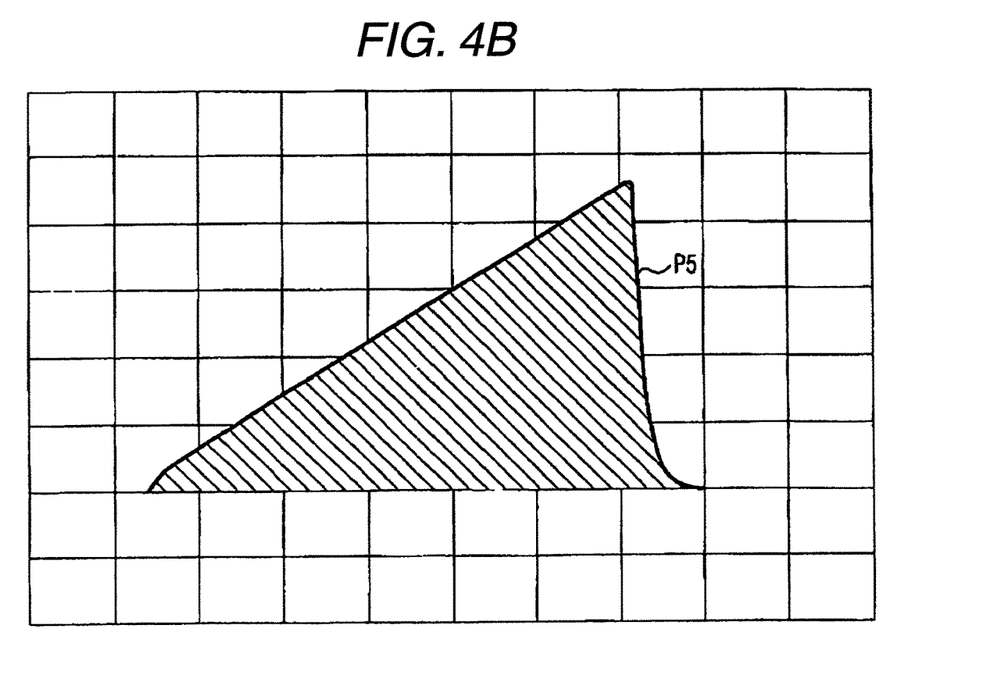
FIG. 4B is a view showing an area (total stimulation intensity) surrounded by a pulse signal and a time axis in the pain sensory nerve stimulation apparatus.

Moreover, the shape of the pulse may be designated by means of the area of the region which is surrounded by the waveform shape of the pulse signal and the time axis. In the pulse P5, for example, the area of the region which is surrounded by the waveform shape of the pulse signal and the time axis means the hatched region in FIG. 4B. The region surrounded by the shape of the applied current of a designated preferred pulse signal and the time axis has an area of 0.01 to 100 (ms·mA). The region surrounded by the shape of the applied voltage of a designated preferred pulse signal and the time axis has an area of 0.1 to 20,000 (ms·V).

The pulse waveform controlling unit 13 disposed in the pulse generation main unit 10 changes the pulse duration, pulse interval, and pulse number of the pulse signal supplied from the pulse signal supplying unit 11. As shown in FIG. 3, the operating portion 24 includes pulse waveform instructing unit 43. The pulse waveform instructing unit 43 can give instructions for causing the pulse waveform controlling unit 13 to change the pulse signal to have a desired pulse duration, pulse interval, and pulse number.

The pulse signal can be selected by means of the pulse duration, the pulse interval, and the pulse number. The pulse duration in the range of 0.5 to 30 ms can be selected at, for example, 0.1 ms intervals, the pulse interval in the range of 1 to 100 ms can be selected at, for example, 1 ms intervals, and the pulse number can be selected at, for example, each interval.

The current/voltage controlling portion 21 connected to the pulse generation main unit 10 is configured to change at least one of the voltage and current of the pulse signal supplied from the pulse signal supplying unit 11. As shown in FIG. 3, the operating portion 24 includes a stimulation intensity instructing unit 42. The stimulation intensity instructing unit 42 can give instructions for causing the current/voltage controlling portion 21 to change the pulse signal to have a desired voltage or current.

In the case of the current control, for example, the current/voltage controlling portion is configured so that the current can be raised from 0.0 mA at 0.01 mA intervals to a predetermined value (also can be lowered from a desired value). After the needle electrode 31 and the contact electrode 32 are attached, the inter-electrode impedance is seemed to be constant. Therefore, it is a matter of course that the portion may be configured so that the voltage can be raised from a predetermined value (for example, 0 V) at 0.2 V intervals to another predetermined value (also can be lowered from a desired value).

The polarity switching portion 25 connected to the current/voltage controlling portion 21 is configured to convert between the electrical polarity of the needle electrode 31 and that of the contact electrode 32. As shown in FIG. 3, the operating portion 24 includes a polarity conversion instructing unit 44. The polarity conversion instructing unit 44 can give instructions for causing the polarity switching portion 25 to convert the electrical polarity. According to the configuration, the electrical polarity of the needle electrode 31 can be set as anode, and that of the contact electrode 32 can be set as cathode, or, by contrast, the electrical polarity of the needle electrode 31 can be set as cathode, and that of the contact electrode 32 can be set as anode.

Character information produced by the pulse generation main unit 10, such as the present stimulation intensity (mA), the rise time, fall time, pulse duration, pulse interval, and pulse number of the pulse signal, and the polarities of the electrodes can be displayed on the displaying portion 23.

The thus configured pain sensory nerve stimulation apparatus is used in the following manner. First, the intraepidermal stimulation electrode portion 30 is contacted with the skin in the test area of the subject, and fixed thereto so that the needle electrode 31 is inserted into the skin. At this time, the needle electrode 31 is inserted into the skin by a depth of about 0.01 to 0.3 mm. Next, the operating portion 24 is operated so as to cause the polarity conversion instructing unit 44 to give instructions for setting the electrical polarity of the needle electrode 31 as anode, and that of the contact electrode 32 as cathode. As a result, the polarity switching portion 25 controls the connection of current paths so that the electrical polarity of the needle electrode 31 is set as anode, and that of the contact electrode 32 is set as cathode.

The operating portion 24 is further operated so as to cause: the rise/fall time instructing unit 41 to give an instruction input for causing the rise/fall time controlling unit 12 to change the pulse signal to have desired rise and fall times; the pulse waveform instructing unit 43 to give instructions for causing the pulse waveform controlling unit 13 to change the pulse signal to have a desired pulse duration, pulse interval, and pulse number; and the stimulation intensity instructing unit 42 to give instructions for causing the current/voltage controlling portion 21 to change the pulse signal to have a desired current or voltage. From the display on the displaying portion 23, it is checked that desired settings are performed by the operating portion 24, and an operation of starting stimulation is then performed.

As described above, the pulse signal is applied between the needle electrode 31 and the contact electrode 32 to perform stimulation. In this state, the operating portion 24 is operated so as to gradually increase the current value (or the voltage value) until the subject feels pain. Alternatively, measurement may be conducted while the rise and fall times are changed, or while the pulse duration, the pulse interval, and the pulse number are changed. If the subject has a nervous disorder, this can be determined from a phenomenon that the subject does not feel pain, or that, even the subject feels pain, stimulation of higher intensity is required. Moreover, the intraepidermal stimulation electrode portion 30 is contacted with the skin in another (or the identical) test area of the subject, so that differences depending on the stimulation position, a difference between right and left body portions, and the like can be checked. When the operating portion 24 is operated so as to convert the electrical polarities of the needle electrode 31 and the contact electrode 32 and then measurements are conducted in the same manner as described above, also knowing of progression of and adequate control of a diabetic nervous disorder can be checked.

Measurement Example 1

While the above-described pain sensory nerve stimulation apparatus was used, the electrical polarity of the needle electrode 31 was set as anode, and that of the contact electrode 32 was set as cathode, stimulation was performed under the following conditions, and the somatosensory evoked potential was measured.

Subject: healthy 26-year old adult male,

Stimulation conditions: constant-current stimulation by a pulse signal having a pulse duration of 0.5 ms, Stimulation portion: anterior part of the forearm around the wrist, Pulse signal: intensity of 0.07 mA, pulse interval of 20 ms, pulse duration of 0.5 ms, pulse number of 5, rising of 0.68 ms in the rectilinear mode, and falling of 0.068 ms, and Number of averaging: ten.

Figure 5:
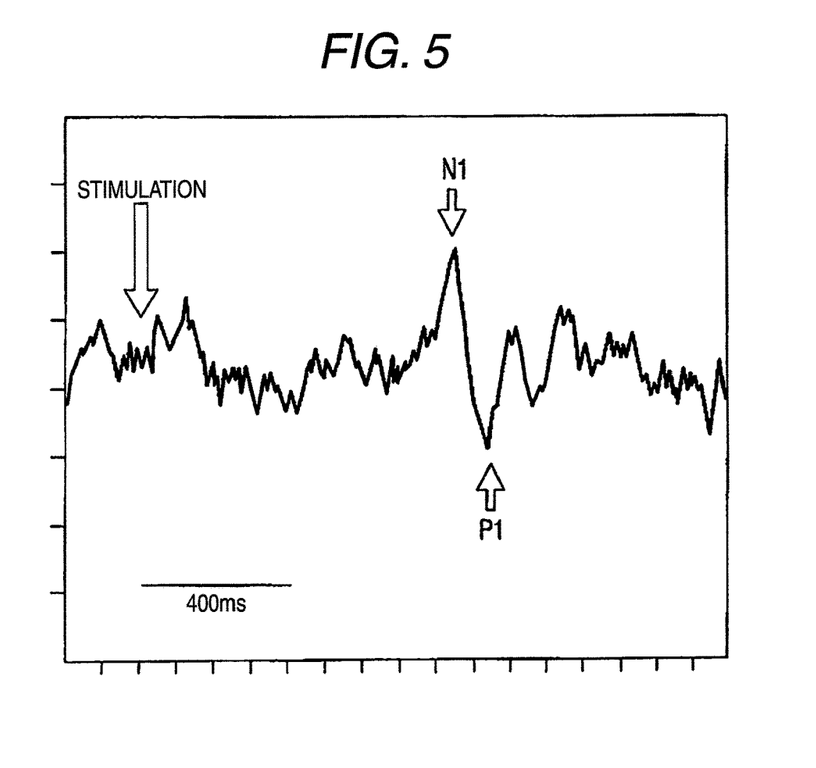
FIG. 5 is a view showing a first measurement result in the case where stimulation on C fibers is performed in the pain sensory nerve stimulation apparatus.

In the case where stimulation was performed while the stimulation current was set to 0.07 mA as described above, as shown in FIG. 5, the somatosensory evoked potential has a negative peak (N1) at 850 ms following stimulation, and a positive peak (P1) at 950 ms. The distance from the stimulation portion to the brain is about 110 cm. When the conduction velocity is calculated using the N1 peak latency, the conduction velocity is about 1.3 m/s. The calculated velocity is within the range of the conduction velocity C fibers, or 0.5 to 2 m/s. The value is obviously different from the conduction velocity of Aδ fibers (15 m/s). Considering the conduction distance, it is unlikely that signals ascending through Aδ fibers contributed to shape the N1-P1 responses at this latency (the time period from application of stimulation to response). As a result, it was proved that only C fibers are stimulated. This stimulation of only C fibers was enabled by employing the electrode polarity configuration in which the electrical polarity of the needle electrode 31 is set to the anode and that of the contact electrode 32 is set to the cathode, and which cannot be conceived from the related-art technique.

Measurement Example 2

While the above-described pain sensory nerve stimulation apparatus was used, two intraepidermal stimulation electrode portions 30 were used, the electrical polarity of the needle electrode 31 was set as the anode, and that of the contact electrode 32 was set as the cathode, stimulation was performed under the following conditions, and the somatosensory evoked potential was measured.

Subject: healthy 45-year old adult male,

Stimulation conditions: constant-current stimulation by a pulse signal having a stimulation duration of 20 ms, Stimulation portion: levels of the dorsum of the left hand and the elbow of the forearm, Pulse signal: intensity of 0.05 mA (hand dorsum) and 0.03 mA (elbow), pulse interval of 30 ms, pulse duration of 20 ms, pulse number of 4, rising in the exponential mode, and falling of 0.025 ms, and Number of averaging: twelve.

Figure 6:
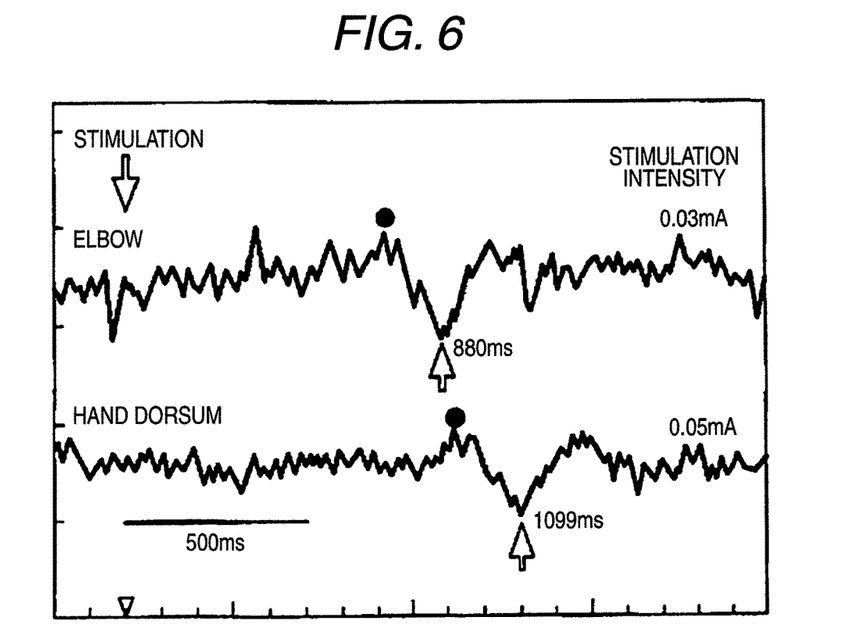
FIG. 6 is a view showing a second measurement result in the case where stimulation on C fibers is performed in the pain sensory nerve stimulation apparatus.

In the case where stimulation was performed while the stimulation current was set to 0.05 mA for the hand dorsum and 0.03 mA for the forearm as described above, as shown in FIG. 6, the somatosensory evoked potentials are similar to each other. The evoked positive peak (P2) latency (the arrows of FIG. 6) is 1,099 ms in the stimulation of the hand dorsum, and 880 ms in the stimulation of the forearm, and the latency difference of the stimulations is 219 ms. The distance between the two stimulation portions is 24.5 cm. Therefore, the peripheral conduction velocity is calculated to be 1.1 m/s. In the recording example, also a negative component (N2) preceding P2 is recorded (the circle in FIG. 6). A similar calculation shows that the conduction velocity is 1.2 m/s. Both the calculated velocities are within the range of the conduction velocity due to C fiber stimulation, or 0.5 to 2 m/s. A conduction velocity component due to Aδ fiber stimulation appears in the range of 300 to 400 ms. Also from this point of view, it is apparent that the responses obtained in the example are not due to Aδ fibers. Therefore, it was proved that only C fibers are stimulated. This stimulation of only C fibers was enabled by employing the electrode polarity configuration in which the electrical polarity of the needle electrode 31 is set to the anode and that of the contact electrode 32 is set to the cathode, and which cannot be conceived from the related-art technique.

Measurement Example 3

The above-described pain sensory nerve stimulation apparatus was used, one intraepidermal stimulation electrode portion 30 was used, the electrical polarity of the needle electrode 31 was set as the cathode, and that of the contact electrode 32 was set as the anode. Namely, the operating portion 24 was operated so that the polarity was switched by the polarity conversion instructing unit 44. Stimulation was performed under the following conditions, and the somatosensory evoked potential was measured. The illustrated example was obtained by recording C fiber responses following the dorsum stimulation in Measurement example 2 above, and thereafter inverting only the stimulation polarity while maintaining the electrodes and the stimulation settings as they are.

Subject: healthy 45-year old adult male,

Pulse signal: intensity of 0.05 mA, pulse interval of 30 ms, pulse duration of 20 ms, pulse number of 4, rising in the exponential mode, and falling of 0.025 ms, and Number of averaging: twenty.

Figure 7:
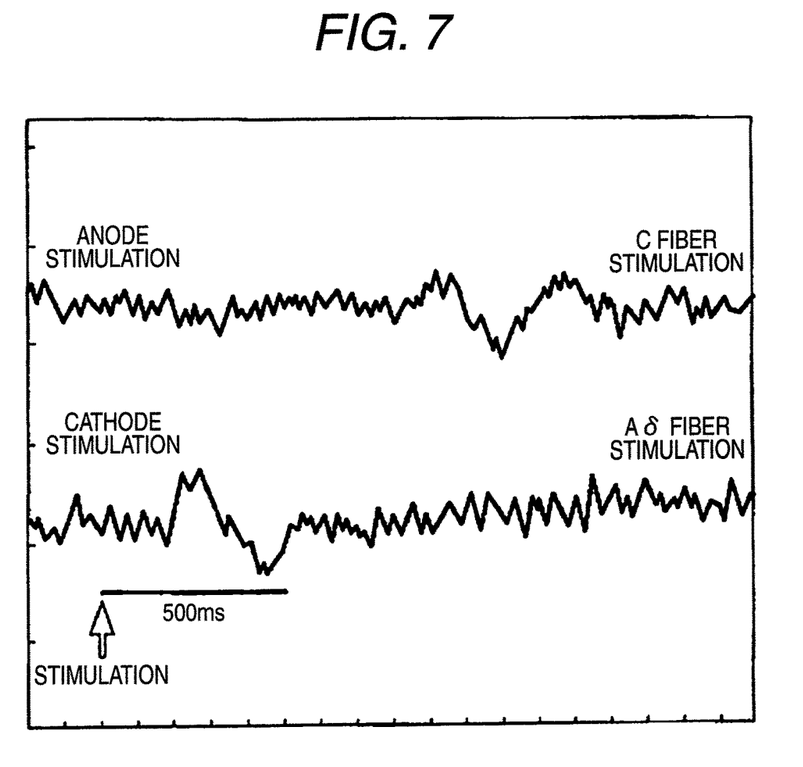
FIG. 7 is a view showing a third measurement result in the case where stimulation is performed while electrical polarities are inverted in the pain sensory nerve stimulation apparatus.

In the case where stimulation was performed while the stimulation current was set to 0.05 mA as described above, as shown in FIG. 7 (lower stage), negative and positive peaks were produced in the range of 200 to 400 ms after stimulation, in the somatosensory evoked potential. Unlike prolonged pain (slight long-term pain) in the case of the anodal stimulation, pricking pain was caused in the case of the cathodal stimulation. A C fiber nociceptors relates to steady or burning pain which is typified by inflammation, and an Aδ fiber nociceptors controls sharp pain. Therefore, it is considered that Aδ fibers are stimulated by the cathode stimulation. It is well known that, in the hand dorsum stimulation, negative and positive components are evoked in the range of 200 to 400 ms by Aδ fiber stimulation. This example is strictly coincident with the knowing. In the waveform of FIG. 7, it is important that, although the conditions except the polarity inversion are identical, C fibers and Aδ fibers are independently stimulated. In the anode stimulation (upper trace), components in the range of 200 to 400 ms are not observed, and, in the cathode stimulation (lower trace), no C fiber response in the vicinity of 1,000 ms is evoked. It was proved that, in selective stimulation of skin sensation fibers, a very remarkable polarity inversion effect can be obtained.

Consequently, it was proved that C fibers and Aδ fibers can be independently stimulated. Therefore, there are an effect that it is possible to check a nervous disorder which is due to only C fibers, and the occurrence of which is to be initially known, and another effect that it is possible to check whether the nervous disorder progresses to Aδ fibers or not, and the progress state of the disorder can be known. In Measurement examples 1 to 3, a peak is not observed in a range from stimulation corresponding to Aβ fibers relating to the tactile sensations, to the vicinity of 20 ms (where the distance from the stimulation portion to the derivation portion is about 110 cm, and the conduction velocity relating to Aβ fibers is about 50 m/s). Therefore, it was checked that only the pain sensations could be selectively stimulated without stimulating the tactile sensations.

In Measurement examples 1 to 3, the SEPs was obtained in order to quantitatively prove that only C fibers are stimulated. When an actual nervous disorder is to be checked, however, the above-described stimulation may be applied to the subject, and the nervous disorder may be checked by asking the subject whether the stimulation is felt or not. In the pulse signal to be applied in one stimulation, the current level is very low or about 0.1 mA. The time of stimulation on the subject is about 0.1 sec. This time can be said very short.

Measurement Example 4

While the above-described pain sensory nerve stimulation apparatus was used, two intraepidermal stimulation electrode portions 30 were used, the electrical polarity of the needle electrode 31 was set as the anode, and that of the contact electrode 32 was set as the cathode, stimulation was performed under the following conditions, and the somatosensory evoked potential was measured.

Subject: healthy 45-year old adult male,

Stimulation conditions: constant-current stimulation by a pulse signal having a stimulation duration of 20 ms, Stimulation portion: levels of the dorsum of the right foot and the front face of the knee of the lower leg, Pulse signal: intensity of 0.08 mA (dorsum) and 0.03 mA (knee), pulse interval of 30 ms, pulse duration of 20 ms, pulse number of 3, rising of 20 ms in the exponential mode, falling of 0.025 ms, and Number of averaging: twelve. The subject performed the task that, when the subject feels stimulation, the subject pressed a button as quickly as possible, and the response time (the time between the stimulation and the button pressing) was simultaneously recorded.

Figure 8A:
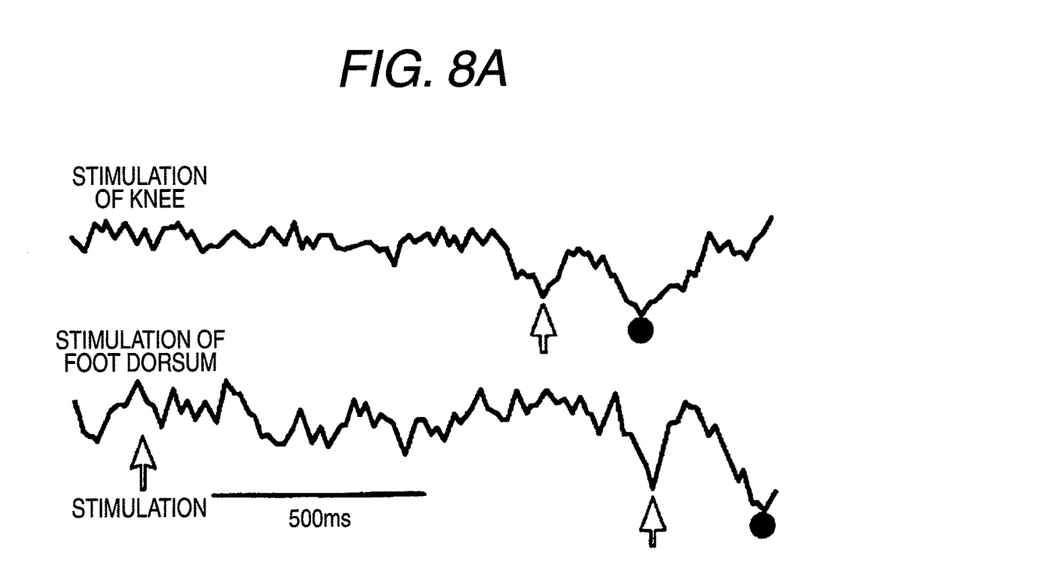
FIG. 8A is a view showing a fourth measurement result in the case where stimulation on C fibers is performed in the pain sensory nerve stimulation apparatus.

In the case where stimulation was performed while the stimulation current was set to 0.05 mA for the dorsum of the foot and 0.03 mA for the knee as described above, as shown in FIG. 7, the somatosensory evoked potentials are similar to each other. The evoked positive peak (P2) latency (the arrows of FIG. 8A) is 1,452 ms in the stimulation of the foot dorsum, and 1,135 ms in the stimulation of the knee, and the latency difference of the stimulations is 317 ms. The distance between the two stimulation portions is 35 cm. Therefore, the velocity of the peripheral conduction between the stimulation portions is calculated to be 1.1 m/s. In the recording example, also a slower positive component (the solid circle in FIG. 8A) which seems to be caused by the button pressing task) is recorded, and the latency difference of the stimulation portions is 311 ms. A similar calculation shows that the conduction velocity is 1.1 m/s. The calculated velocity is within the range of the conduction velocity due to C fiber stimulation, or 0.5 to 2 m/s. Therefore, it was proved that stimulation of only C fibers was enabled also with respect to the lower limb.

Figure 8B:
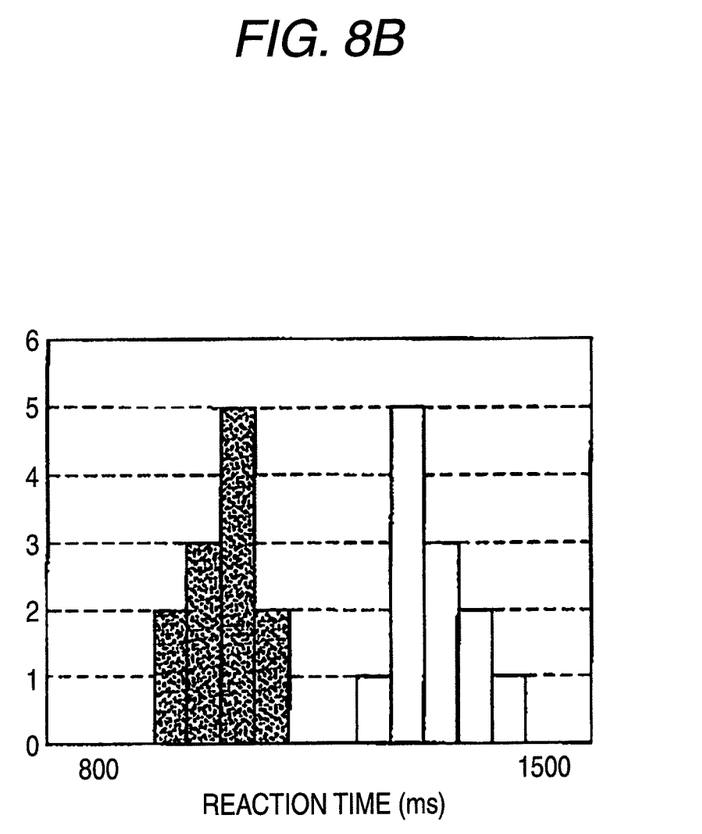
FIG. 8B is a view showing response times for respective stimulation portions in the fourth measurement result in the case where stimulation on C fibers is performed in the pain sensory nerve stimulation apparatus.

The graph of FIG. 8B shows the response times which were simultaneously recorded, the blank bars show the response time of the foot dorsum, and the bars of a small-dot pattern show that of the knee. The response times are divided into blocks of 50 ms, and the number of responses in each block is shown in form of a bar graph. The average response time of the foot dorsum was 1,263±61 ms, and that of the knee was 956±43 ms. Therefore, the response time difference between the stimulation portions is 309 ms, and the conduction velocity is calculated to be 1.1 m/s. Usually, the measurement of the response time based on the button pressing produces a large error, and is difficult to be used in the case of a short latency, but seems to be sufficiently used in the case where a response of about 1 sec. is to be checked. In the case where the measurement is used in checking of a nervous disorder, even when the evoked potential and a correct response time are not measured, the measurement can be sufficiently performed by simply giving a signal of "Yes" as soon as the subject feels the stimulation, because, when a response is produced in a latency zone of about 1 sec. or slower, it is certain that the subject feels a sensations due to C fiber stimulation under the stimulation conditions.

Measurement Example 5

Next, results of measurements which were conducted while changing various conditions of the pulse signal are described. In all the measurements, the response time of the same subject (45-year old adult male) was measured, and the stimulation portion was the dorsum of the left hand. FIG. 9A shows an effect of the polarity inversion while the stimulation conditions except the polarity are identical (the pulse is exponential, the pulse duration is 20 ms, the stimulation interval is 30 ms, and the pulse number is 3). When the stimulation intensity was started from 0.01 mA and increased in a step 0.01 mA, burning pain was not felt in the case of the anode stimulation until the stimulation intensity was 0.05 mA, and at this time the response time was 872 ms. It is apparent that this is a result of C fiber stimulation. In the graph above, the left-most plots show the reaction time in response to C fiber stimulation. When the response time is plotted while the stimulation is thereafter similarly increased in the step of 0.01 mA, the response time is suddenly shortened in the vicinity of 0.2 mA, and stabilized to about 260 to 320 ms. The evoked sensation at this time is clear pricking pain because Aδ fibers are stimulated. When the stimulation is further increased, a tapping tactile sensation is added in the vicinity of 0.6 mA, and the response time is about 200 to 220 ms because Aβ fibers related to the tactile sensations are recruited. In the case of the hand dorsum, it is said that the difference between the Aδ and Aβ fiber signals in time of arrival at the brain is 60 ms. The result coincides with this. In the cathode stimulation (the lower graph of FIG. 9A), by contrast, the response time of C fiber stimulation is not observed at any stimulation intensity, and the response range of Aδ fibers is slightly wider (Aδ fibers in 0.06 mA or larger).

In the result, the following point is important. In the case where anode stimulation is performed by using the pain sensory nerve stimulation apparatus, respective nerve fibers are stimulated in the order opposite to the excitability order (Aβ, Aδ, and C) in the related-art electrical stimulation. Under the stimulation conditions, C fibers can be selectively stimulated at a weak stimulation intensity. It is obvious that this is advantageous.

Figure 9B:
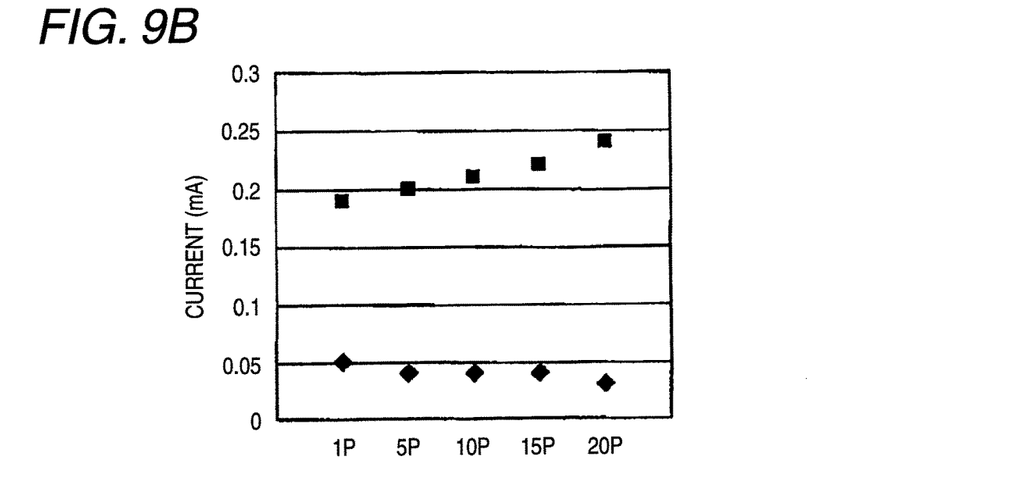
FIG. 9B is a view showing relationships between a rise time and stimulation intensity in the pain sensory nerve stimulation apparatus.

FIG. 9B shows a study of the effect of the pulse rising under the same stimulation conditions except of the setting of the rising (the falling is 17.5 μs, the pulse duration is 1 to 1.5 ms, and the pulse number in the case of the pulse interval of 30 ms is 5). In FIG. 9B, the abscissa indicates the rise time, 1 P=17.5 μs, 5 P=194 μs, 10 P=433 μs, 15 P=688 μs, and 20 P=987 μs. The plot points indicated by a rhomboid show the threshold of C fiber stimulation, and those indicated by a square show the limit value of C fiber stimulation. The area between the rhomboid plot points and the square plot points is the effective region where C fiber stimulation can be effectively performed. The pulse duration was somewhat adjusted for each conditions so that the total stimulation intensity (current×time) was constant. As shown in the graph of FIG. 9B, when the rise time is set to be long, the threshold of C fiber stimulation is decreased, and the limit value of C fiber stimulation is raised, or namely the effective stimulation region of C fiber selective stimulation (between the threshold of C fiber stimulation and the limit value of C fiber stimulation) is widened.

Figure 9C:
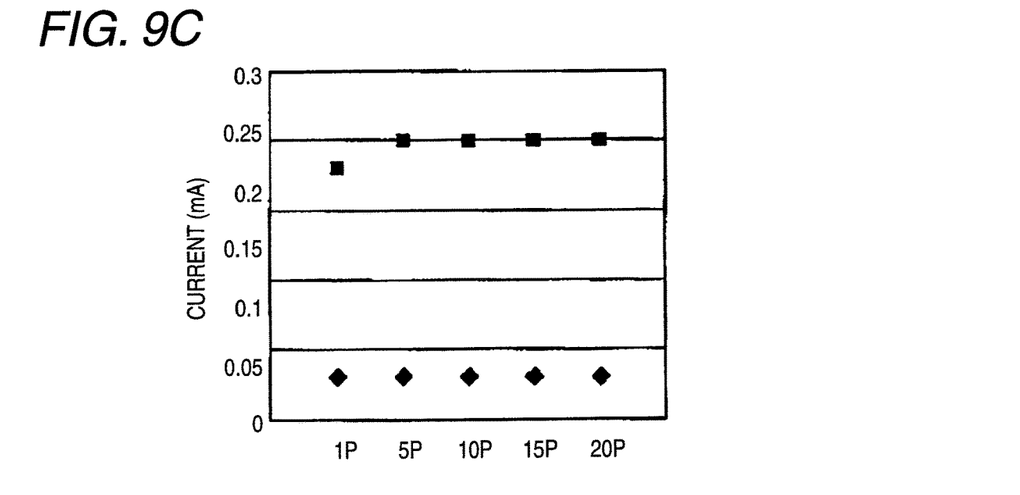
FIG. 9C is a view showing relationships between a fall time and stimulation intensity in the pain sensory nerve stimulation apparatus.

Similarly, FIG. 9C shows a study of the effect of the fall time in the case where the total stimulation intensity is constant. Stimulation conditions (the falling is 17.5 μs, the pulse duration is 0.5 to 1.0 ms, and the pulse number in the case of the pulse interval of 30 ms is 5) were employed. In FIG. 9C, the abscissa indicates the fall time, 1 P=17.5 μs, 5 P=194 μs, 10 P=433 μs, 15 P=688 μs, and 20 P=987 μs. The plot points indicated by a rhomboid show the threshold of C fiber stimulation, and those indicated by a square show the limit value of C fiber stimulation. The area between the rhomboid plot points and the square plot points is the effective C fiber stimulation region where C fiber stimulation can be effectively performed. Although the fall time is not so noticeable as the rise time, also the fall time affects the effective C fiber stimulation region. From these results, it is obvious that the shape of the pulse waveform affects C fiber stimulation.

Although individual differences exist and results are slightly different between measurements, generally, the Aδ fiber selectivity is higher as the rising and the falling are steeper, and the C fiber selectivity is higher as the rising and the falling are gentler. Among pulse waveforms which are used in a related art, for example, it is expected that a square wave is suitable for Aδ fiber stimulation, and a triangular or sawtooth wave is suitable for C fiber stimulation.

Figure 9D:
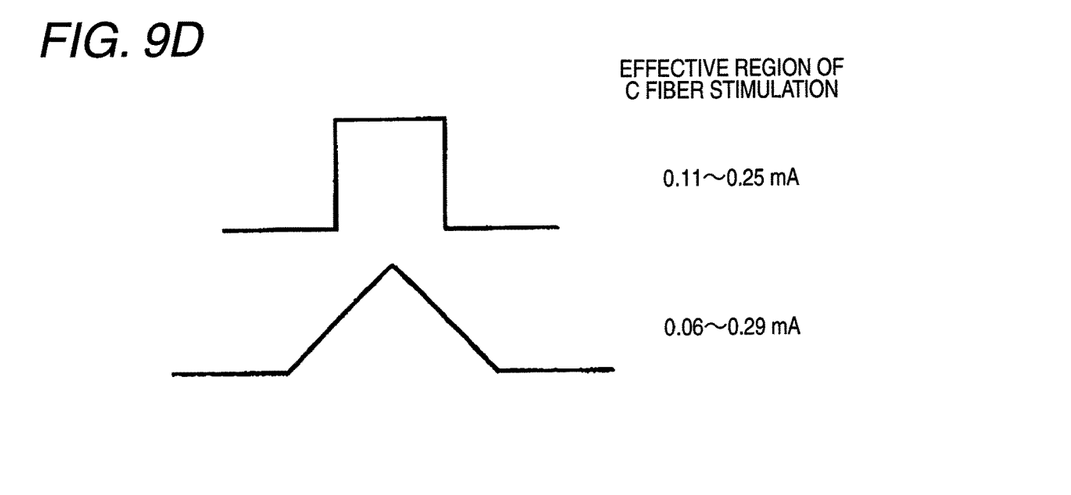
FIG. 9D is a view in which a square wave and a triangular wave are compared while total stimulation intensity is made constant in the pain sensory nerve stimulation apparatus.
Figure 9E:
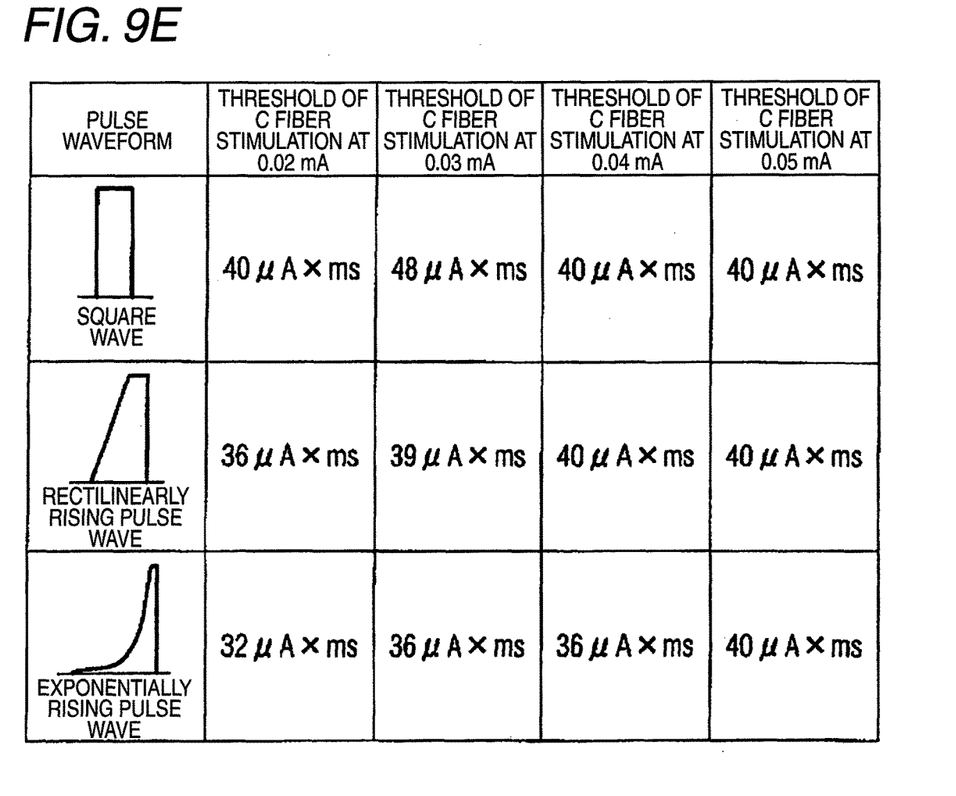
FIG. 9E is a view in which transition of total stimulation intensity in the case where stimulation current is changed with respect to a square wave, a triangular wave, and an exponentially waveform in the pain sensory nerve stimulation apparatus.

FIG. 9D shows a comparison between square and triangular pulses in the case where the total stimulation intensity is constant. Stimulation conditions for a square wave (the rising is 17.5 μs the falling is 17.5 μs and the pulse duration is 0.5 ms), and those for a triangular wave (the rising is 500 μs, the falling is 500 μs, and the pulse duration is 1 ms) were employed. The current region (effective C fiber stimulation region) where C fibers are selectively stimulated is 0.11 to 0.25 mA for the square wave, and 0.06 to 0.29 mA for the triangular wave. It is known that a triangular wave is effective in expanding the effective C fiber stimulation region. From this result, it is expected that a pulse waveform in which the rising is gentler than that of a square wave is advantageous from the viewpoint of the total stimulation intensity.

FIG. 9E shows measurement results showing the above. The pulse duration (threshold) in which C fibers are first stimulated at a certain current value is obtained by three waveforms, or a square wave, a rectilinearly rising waveform (the rising: 1 ms), and an exponentially rising waveform, the total stimulation intensities (ms·mA) were calculated from the pulse shape and the current value, and the values of the total stimulation intensities were compared with one another. Stimulation conditions (the falling is 25 μs, the rising of the square wave is 17.5 μs, the rising of the rectilinearly rising waveform is 1 ms, the pulse duration is 20 ms, and the pulse number is 3) were employed. As shown in FIG. 9E, it is seen that, in order to obtain the same C fiber stimulation effect, the exponentially waveform requires the least total stimulation intensity. At the threshold of 0.02 mA, for example, the total stimulation intensity in the case of the exponentially waveform is smaller by 20% than that in the case of the square wave.

Figure 9F:
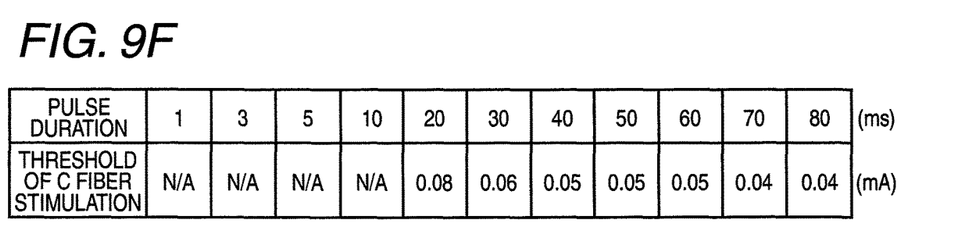
FIG. 9F is a view showing relationships between a pulse duration and stimulation intensity in the pain sensory nerve stimulation apparatus.

FIG. 9F shows the effect of the extension of the pulse duration in experiment examples in which C fibers could not be stimulated by a short pulse. Stimulation conditions (the falling and rising are 17.5 μs, the stimulation interval is 83 ms, and the pulse number is 5) were employed. In the illustrated examples, the C fiber stimulation effect is not observed before the pulse duration of 10 ms, and first appears at 20 ms, and, when the pulse duration is further extended, the threshold of C fiber stimulation is slightly lowered.

Figure 9G:
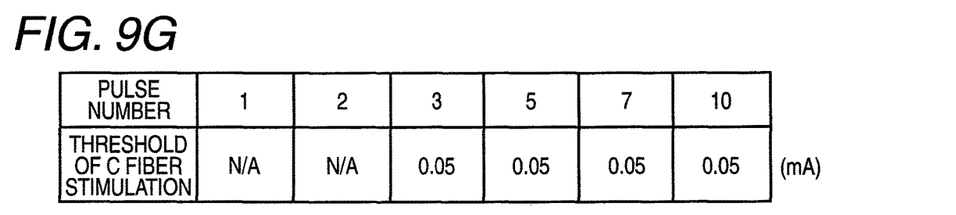
FIG. 9G is a view showing relationships between a pulse number and stimulation intensity in the pain sensory nerve stimulation apparatus.

FIG. 9G shows the effect of the increase of the pulse number in experiment examples in which C fibers could not be stimulated by single stimulation. Stimulation conditions (the falling and rising are 25 μs, the pulse duration is 40 ms, and the stimulation interval is 80 ms) were employed. In the pulse numbers of 1 and 2, C fibers were not stimulated, and, in the pulse numbers of 3 to 10, a clear stimulation sensation of C fibers was evoked. In the pulse numbers of 3 to 10, the threshold was not changed. The response time is substantially constant (980 to 1,120 ms) irrespective of the pulse number, and it seems that, at any pulse number, the button was pressed in response to the third stimulation.

As apparent from these results, all of the conditions of the pulse application affect selective stimulation of C or Aδ fibers. It is apparent that, in order to the optimum values of the parameters and the optimum combination of the conditions to be enabled in respective test examples, the function of the stimulation apparatus of the invention is essential. Particularly, the free settings of the polarity inversion, and the rising and falling of the pulse waveform are important. Also the settings of the other functions such as setting of the current and the voltage are essential. In all the measurement examples of FIGS. 9A to 9G, it is apparent that an accuracy in an order of 0.01 mA is necessary in C fiber stimulation. From this result, C fibers and Aδ fibers can be selectively stimulated. Particularly, stimulation can be performed as described above by using a pulse wave which is different from a sine wave. These effects seem to be useful in early detection and functional assessment of a nervous disorder.

In the above-described embodiment and measurement examples, it is a matter of course that a configuration in which a plurality of intraepidermal stimulation electrode portions 30 are disposed may be employed and used.

According to an aspect of the invention, the pulse signal is supplied while the electrical polarity of the first electrode is set as the anode, and that of the second electrode is set as the cathode, and hence pulses which stimulate only C fibers having the thinnest fiber diameter can be supplied. The first electrode has a needle-like shape, and hence the area contacting with a living body is very smaller than that of the second electrode. Therefore, there is a possibility that C fibers which are thinner than Aδ fibers cannot be adequately excited. This is caused mainly by the fact that smaller fibers have a higher threshold with respect to electrical stimulation. By contrast, C fibers have possibly available physical properties such as that the distribution density is higher than Aδ fibers, that the fibers run perpendicularly to the skin surface, and that the fibers extend to the surface part as compared with ends of mechanoreceptors. Therefore, stimulation of only C fibers is enabled by the idea which is opposite to that of the related-art technique in which a signal is applied while a stimulation portion is set to the cathode. These effects can be easily proved by results of measurements of the stimulation sensations, the response time, and the waveform of the somatosensory evoked potential (SEPs), as described above. When a sensation of burning pain which is typified by inflammation is caused, the response time is very slow or about 1,000 ms in stimulation on, for example, a hand. In SEPs data, it is found that the response time (latency) from the stimulation to the peak becomes a time corresponding to the conduction velocity of C fibers. It is found that only C fibers can be stimulated without substantially affecting other nerve fibers.

According to an aspect of the invention, at least one of rise and fall times of the supplied pulse signal, in which the electrical polarity of the first electrode is set as the anode and the electrical polarity of the second electrode is set as the cathode, is changed, so that the pulse supply in which only C fibers having the smallest diameter are stimulated without substantially affecting other nerve fibers can be performed.

According to an aspect of the invention, also Aδ fibers and Aβ fibers which are larger nerve fibers can be stimulated by changing at least one of the voltage and current of the pulse signal to change the stimulation intensity.

When the stimulation intensity is changed, respective nerve fibers can be stimulated in the order which is opposite to the excitability order (Aβ, Aδ, and C) in the related-art electrical stimulation. Particularly, C fibers can be selectively stimulated at a weak stimulation intensity.

According to an aspect of the invention, since the pulse duration, pulse interval, and pulse number of the pulse signal can be changed, a measurement which absorbs individual differences can be performed while searching the pulse duration, pulse interval, and pulse number at which stimulation of C fibers is enabled.

A nervous disorder can be checked depending on whether, when pain sensory nerves are stimulated, the subject feels the stimulation or not. According to an aspect of the invention, stimulation to be applied to the subject is performed in a very short period of time and at a very low level, and moreover exerts no influence on other nerve fibers. Therefore, a nervous disorder can be checked rapidly and efficiently while imposing a minimal burden on the subject.

According to an aspect of the invention, when the electrical polarity is converted between the electrical polarity of the first electrode and that of the second electrode, therefore, stimulations of Aδ fibers and C fibers can be switched over. A nervous disorder is generated from small fibers. When nerve fibers are individually stimulated, early detection, knowing of progression, and functional assessment of a nervous disorder are enabled, thereby largely contributing to knowing of progression of and adequate control of a diabetic nervous disorder.

Even when stimulation is performed on a part of nerve fibers, effects and responses caused by stimulations are identical with one another. In the case where the electrode portion is singly used, there is a possibility that C fibers cannot be accurately stimulated depending on the skill of the operator. When a plurality of electrode portions are used, only C fibers can be stimulated irrespective of the skill of the operator.

What is claimed is:

1. A pain sensory nerve stimulation apparatus comprising:
   an electrode portion including:
      a first electrode, a tip end of which is adapted to be inserted into a skin; and
      at least one second electrode which is disposed in a circumference of the first electrode without being electrically conductive with the first electrode, and which is adapted to be in contact with a skin;
   a pulse signal supplier, supplying a pulse signal in which an electrical polarity of the first electrode is set as an anode and an electrical polarity of the second electrode is set as a cathode; and
   a stimulation intensity controller configured to deliver stimulation parameters to the first electrode and the second electrode which stimulate Aδ fibers and C fibers independently,
   wherein the stimulation intensity controller is configured to deliver the stimulation parameters to the first electrode and the second electrode which stimulate the Aδ fibers and the C fibers independently when the first electrode is set as the anode and the second electrode is set as the cathode.

2. The pain sensory nerve stimulation apparatus according to claim 1, further comprising:
   a rise/fall time controller, changing at least one of a rise time and a fall time of the pulse signal.

3. The pain sensory nerve stimulation apparatus according to claim 2, wherein
   at least one of rising and falling of the pulse signal is changed so as to have a rectilinear inclined shape.

4. The pain sensory nerve stimulation apparatus according to claim 2, wherein
   at least one of rising and falling of the pulse signal is changed so as to have an exponential shape.

5. The pain sensory nerve stimulation apparatus according to claim 1, further comprising:
   a pulse waveform controller, changing at least one of a pulse duration, a pulse interval, and a pulse number of the pulse signal.

6. The pain sensory nerve stimulation apparatus according to claim 1, wherein
   the pulse signal has a pulse duration of 0.1 to 100 ms.

7. The pain sensory nerve stimulation apparatus according to claim 1, wherein
   a region surrounded by a waveform shape of the pulse signal and a time axis has an area of 0.01 to 100 (ms·mA).

8. The pain sensory nerve stimulation apparatus according to claim 1, wherein
a region surrounded by a waveform shape of the pulse signal and a time axis has an area of 0.1 to 20,000 (ms·V).

9. The pain sensory nerve stimulation apparatus according to claim 1, further comprising:
an electrical polarity converter, converting between the electrical polarity of the first electrode and the electrical polarity of the second electrode.

10. The pain sensory nerve stimulation apparatus according to claim 1, wherein
the second electrode is annularly disposed in the circumference of the first electrode.

11. The pain sensory nerve stimulation apparatus according to claim 1, comprising a plurality of the electrode portion.

12. The pain sensory nerve stimulation apparatus according to claim 1, wherein the first electrode is a needle electrode, and the tip end is configured to insert into an outer surface of the skin which lies underneath the first electrode.

13. The pain sensory nerve stimulation apparatus according to claim 1, wherein a part of the second electrode has a shape which is configured to be inserted into an outer surface of the skin.

14. A pain sensory nerve stimulation apparatus, comprising:
a pulse generation main unit;
a power supplying portion for supplying power to the pulse generation main unit;
an epidermal stimulation electrode portion, which receives a pulse signal from the pulse generation main unit, said epidermal stimulation electrode portion including a first electrode having a tip end adapted to be inserted into a skin and set as an anode, and a second electrode disposed in a circumference of the first electrode adapted to be in contact with a skin and set as a cathode;
a polarity switching portion connected between the pulse generation main unit and the epidermal stimulation electrode portion; and
an operating portion connected to the pulse generation main unit, including a polarity conversion instructing unit configured to instruct the polarity switching portion to invert an electrical polarity of the first electrode and the second electrode and a stimulation intensity controller configured to deliver stimulation parameters to the first electrode and the second electrode which stimulate Aδ fibers and C fibers independently,
wherein the stimulation intensity controller is configured to deliver the stimulation parameters to the first electrode and the second electrode which stimulate the Aδ fibers and the C fibers independently when the first electrode is set as the anode and the second electrode is set as the cathode.

15. The pain sensory nerve stimulation apparatus according to claim 14, wherein the first electrode is a needle electrode, and the tip end is configured to insert into an outer surface of the skin which lies underneath the first electrode.

16. The pain sensory nerve stimulation apparatus according to claim 14, wherein a part of the second electrode has a shape which is configured to be inserted into an outer surface of the skin.

* * * * *